United States Patent
Lehmann

(10) Patent No.: US 7,358,245 B2
(45) Date of Patent: Apr. 15, 2008

(54) TREATMENT OF GASTROESOPHAGEAL REFLUX DISEASE

(75) Inventor: Anders Lehmann, Mölndal (SE)

(73) Assignee: AstraZenca AB, Södertälje (SE)

(*) Notice: Subject to any disclaimer, the term of this patent is extended or adjusted under 35 U.S.C. 154(b) by 272 days.

(21) Appl. No.: 10/496,431

(22) PCT Filed: Nov. 20, 2002

(86) PCT No.: PCT/SE02/02108

§ 371 (c)(1),
(2), (4) Date: May 20, 2004

(87) PCT Pub. No.: WO03/043619

PCT Pub. Date: May 30, 2003

(65) Prior Publication Data

US 2004/0266861 A1    Dec. 30, 2004

(30) Foreign Application Priority Data

Nov. 23, 2001   (SE) .................................... 0103936

(51) Int. Cl.
*A61K 31/05*    (2006.01)
*A61K 31/352*   (2006.01)
*A61K 31/5377*  (2006.01)
*A61K 31/536*   (2006.01)
*A61K 31/473*   (2006.01)

(52) U.S. Cl. ............................... 514/230.2; 514/235.2; 514/298; 514/456; 514/570

(58) Field of Classification Search .............. None
See application file for complete search history.

(56) References Cited

U.S. PATENT DOCUMENTS

| 6,013,648 A | 1/2000 | Rinaldi et al. |
| 2004/0034090 A1 | 2/2004 | Barth et al. |

FOREIGN PATENT DOCUMENTS

| WO | WO-99/57106 | 11/1999 |
| WO | WO-99/60987 | 12/1999 |
| WO | WO-01/24645 A1 | 4/2001 |
| WO | WO-01/32169 A1 | 5/2001 |
| WO | WO-01/41743 A1 | 6/2001 |
| WO | WO-01/96330 A2 | 12/2001 |
| WO | WO-02/365590 A1 | 5/2002 |
| WO | WO-02/47691 A1 | 6/2002 |

OTHER PUBLICATIONS

Stedman's Medical Dictionary, p. 53 (1995).*
www.newswise.com/p/articles/view/511623 (May 9, 2005).*
http://health.yahoo.com/topic/gerd/symptoms/medicaltest/healthwise/popup/str2249(2007).*
http://medgenmed.medscape.com(2007).*
Anders Lehmann et al., "Cannabinoid Receptor Agonism Inhibits Transient Lower Esophageal Sphincter Relaxtions and Reflux in Dogs", Gastroenterology, vol. 123, 2002, pp. 1129-1134.

* cited by examiner

*Primary Examiner*—Phyllis G. Spivack
(74) *Attorney, Agent, or Firm*—White & Case LLP

(57) ABSTRACT

The administration of cannabinoid receptor agonists for inhibition of transient lower esophageal sphincter relaxations, gastroesophageal reflux disease and regurgitation is disclosed.

16 Claims, No Drawings

TREATMENT OF GASTROESOPHAGEAL REFLUX DISEASE

FIELD OF THE INVENTION

The present invention relates to the use of cannabinoid receptor agonists for the inhibition of transient lower esophageal sphincter relaxations. A further aspect of the invention is directed to the use of cannabinoid receptor agonists for the treatment of gastroesophageal reflux disease, as well as for the treatment of regurgitation such as regurgitation in infants, lung disease, chronic laryngitis and asthma.

BACKGROUND OF THE INVENTION

The lower esophageal sphincter (LES) is prone to relaxing intermittently. As a consequence, fluid from the stomach can pass into the esophagus since the mechanical barrier is temporarily lost at such times, an event hereinafter referred to as "reflux".

Gastroesophageal reflux disease (GERD) is the most prevalent upper gastrointestinal tract disease. Current pharmacotherapy aims at reducing gastric acid secretion, or at neutralizing acid in the esophagus. The major mechanism behind reflux has been considered to depend on a hypotonic lower esophageal sphincter. However, e.g. Holloway & Dent (1990) *Gastroenterol. Clin. N. Amer.* 19, pp. 517-535, has shown that most reflux episodes occur during transient lower esophageal sphincter relaxations (TLESRs), i.e. relaxations not triggered by swallows. It has also been shown that gastric acid secretion usually is normal in patients with GERD.

GERD is caused by reflux of gastric contents into the esophagus leading to heartburn and other typical symptoms. In many cases, an inflammation develops in the distal esophagus (esophagitis). It has been known for a long time that suppression of production of gastric acid ameliorates both symptoms and esophagitis. However, some patients continue to have symptoms despite adequate control of acid secretion. Reflux of other noxious factors is believed to be responsible for those symptoms. Most focus has been centered on the importance of bile acids, and the development of severe GERD is related to the degree of esophageal bile acid exposure.

Historically the term cannabinoids referred to the main components of *Cannabis sativa* (marijuana), including about sixty molecules, but this term has been extended to also include endogenous cannabinoids and a wide variety of chemical entities which interact with the two known cannabinoid receptors, CB1 and CB2. Recently, the existence of a previously unknown cannabinoid receptor subtype has been suggested (*Mol. Pharmacol.* (2001), 60: pp. 155-163, *PNAS* (1999), 96: pp. 14136-14141). The cannabinoid receptors belong to the G-protein-coupled superfamily, and the CB1 receptor is expressed predominantly in the central nervous system and to a lesser extent in peripheral tissues (*Nature* (1990), 346: pp. 561-564), whereas the CB2 receptor is located in the periphery and is primarily restricted to cells and tissues associated with immune functions (*Nature* (1993), 365: pp. 61-65).

There are currently four known main chemical groups of cannabinoid receptor agonists:

1) eicosanoids and their analogues, which are animal-derived cannabinoids. Anandamide is one example within this group:

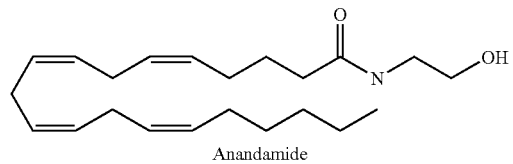

Anandamide 2) classical cannabinoids and their analogues, which are plant-derived cannabinoids, such as $\Delta^9$-THC ($\Delta^9$-tetrahydrocannabinol):

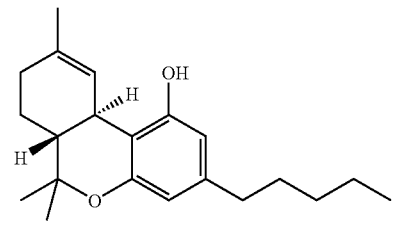

$\Delta^9$-THC 3) non-classical cannabinoids, such as CP 55,940, developed by Pfizer:

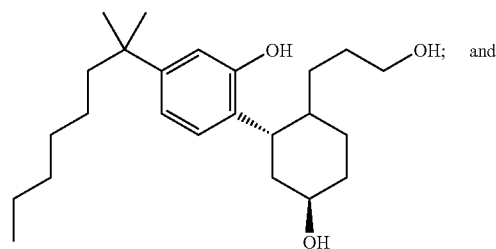

CP 55,940

4) aminoalkylindole cannabinoids such as WIN 55,212-2, developed by Sterling-Winthrop:

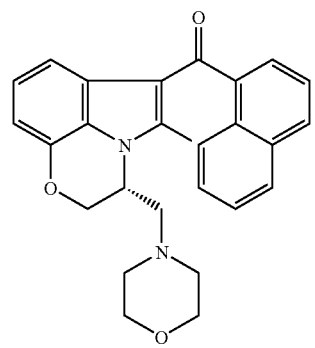

WIN 55,212-2

The only cannabinoids having obtained drug approval so far, belong to the classical cannabinoid family. $\Delta^9$-THC having the generic name Dronabinol, is registered in the United States under the trade mark Marinol®, for use against nausea induced by anticancer drugs and to combat weight loss in AIDS patients by stimulating appetite. Nabilone is a synthetic derivative developed by Eli Lilly (Cesamet®), registered in Canada, UK and Eire for the suppression of nausea and vomiting provoked by cancer chemotherapy.

A pharmacological review on $CB_1$ and $CB_2$ receptor ligands has been disclosed by Pertwee, R. G. in *Curr. Med. Chem.* (1999) 6: pp.635-664. For additional comprehensive reviews see e.g. Barth F. *Exp. Opin. Ther. Patents* (1998) 8(3): pp. 301-313; Pertwee, R. G. *Exp. Opin. Invest. Drugs* (2000) 9(7): pp.1553-1571; Goy, P.; Jagerovic, N. *Exp. Opin. Ther. Patents* (2000) 10(10): pp.1529-1538, as well as references cited therein.

WO 01/32169 of Yissum Research Development, discloses a pharmaceutical composition for treating or preventing inter alia pain, gastrointestinal disorders, and autoimmune diseases, by the administration of specific compounds acting on the CB2 receptor. Inflammatory Bowel Disease (IBD) is one disease for which compounds disclosed therein have been tested.

The object of the present invention was to find a new way for the inhibition of transient lower esophageal sphincter relaxations (TLESRs), thereby preventing reflux. More particularly the object of the invention was to find a new and improved way of treating gastroesophageal reflux disease (GERD), as well as a new and improved way for the treatment of regurgitation such as regurgitation in infants, lung disease, chronic laryngitis and asthma.

Outline of the Invention

It has now surprisingly been found that cannabinoid receptor agonists can be used for the inhibition of transient lower esophageal sphincter relaxations (TLESRs), and thus for the treatment of gastroesophageal reflux disease (GERD).

Consequently, the present invention is directed to the use of a cannabinoid receptor agonist for the manufacture of a medicament for the inhibition of transient lower esophageal sphincter relaxations (TLESRs).

A further aspect of the invention is the use of a cannabinoid receptor agonist for the manufacture of a medicament for the prevention of reflux.

Still a further aspect of the invention is the use of a cannabinoid receptor agonist for the manufacture of a medicament for the treatment of gastroesophageal reflux disease (GERD). Effective management of regurgitation would be an important way of preventing, as well as curing lung disease due to aspiration of regurgitated gastric contents. Thus, a further aspect of the invention is the use of a cannabinoid receptor agonist for the manufacture of a medicament for the treatment or prevention of regurgitation.

Effective management of regurgitation in infants would be an important way of preventing, as well as curing lung disease due to aspiration of regurgitated gastric contents, and for managing failure to thrive, inter alia due to excessive loss of ingested nutrient. Thus, a further aspect of the invention is the use of a cannabinoid receptor agonist for the manufacture of a medicament for the treatment of regurgitation in infants.

Another aspect of the invention is the use of a cannabinoid receptor agonist for the manufacture of a medicament for the management of failure to thrive.

Still a further aspect of the invention is the use of a cannabinoid receptor agonist for the manufacture of a medicament for the treatment or prevention of lung disease. The lung disease to be treated may inter alia be due to aspiration of regurgitated gastric contents.

Another aspect of the invention is the use of a cannabinoid receptor agonist for the manufacture of a medicament for the treatment or prevention of asthma, such as reflux-related asthma.

A further aspect of the invention is the use of a cannabinoid receptor agonist for the manufacture of a medicament for the treatment or prevention of chronic laryngitis.

A further aspect of the present invention is a method for the inhibition of transient lower esophageal sphincter relaxations (TLESRs), whereby a pharmaceutically and pharmacologically effective amount of a cannabinoid receptor agonist is administered to subject in need of such inhibition.

Another aspect of the invention is a method for the prevention of reflux, whereby a pharmaceutically and pharmacologically effective amount of a cannabinoid receptor agonist is administered to a subject in need of such prevention.

Still a further aspect of the invention is a method for the treatment of gastroesophageal reflux disease (GERD), whereby a pharmaceutically and pharmacologically effective amount of a cannabinoid receptor agonist is administered to a subject in need of such treatment.

Another aspect of the present invention is a method for the treatment or prevention of regurgitation, whereby a pharmaceutically and pharmacologically effective amount of a cannabinoid receptor agonist is administered to a subject in need of such treatment.

Yet another aspect of the invention is a method for the treatment or prevention of regurgitation in infants, whereby a pharmaceutically and pharmacologically effective amount of a cannabinoid receptor agonist is administered to a subject in need of such treatment.

Still a further aspect of the invention is a method for the treatment, prevention or inhibition of lung disease, whereby a pharmaceutically and pharmacologically effective amount of a cannabinoid receptor agonist is administered to a subject in need of such treatment. The lung disease to be treated may inter alia be due to aspiration of regurgitated gastric contents.

Still a further aspect of the invention is a method for the management of failure to thrive, whereby a pharmaceutically and pharmacologically effective amount of a cannabinoid receptor agonist is administered to a subject in need of such treatment.

A further aspect of the invention is a method for the treatment or prevention of asthma, such as reflux-related asthma.

A further aspect of the invention is a method for the treatment or prevention of chronic laryngitis.

A further aspect of the invention is the use of a cannabinoid receptor agonist having selectivity for the CB1 receptor, in any one of the indications discussed above. Still a further aspect of the invention is the use of a cannabinoid receptor agonist having selectivity for the CB2 receptor, in any one of the indications discussed above.

For the purpose of this invention, the term "agonist" should be understood as including both full agonists as well as partial agonists, whereby a "partial agonist" should be understood as a compound capable of partially, but not fully, activating cannabinoid receptors.

The wording "cannabinoid receptor agonist" as used herein, includes not only full cannabinoid receptor agonists or partial cannabinoid receptor agonists, but also includes indirect cannabinoid receptor agonists. By the wording "indirect cannabinoid receptor agonist" as used herein is meant inhibitors to the enzyme fatty acid amidohydrolase (FAAH) as well as inhibitors to the enzyme anandamide transporter (ANT). Inhibitors to ANT or FAAH may be useful as indirect cannabinoid receptor agonists by increasing the concentration of endocannabinoids at the cannabinoid receptors, and thus useful for the inhibition of TLESRs.

The wording "TLESR", transient lower esophageal sphincter relaxations, is herein defined in accordance with Mittal, R. K., Holloway, R. H., Penagini, R., Blackshaw, L. A., Dent, J., 1995; *Transient lower esophageal sphincter relaxation. Gastroenterology* 109, pp. 601-610.

The wording "reflux" is defined as fluid from the stomach being able to pass into the esophagus, since the mechanical barrier is temporarily lost at such times.

The wording "GERD", gastroesophageal reflux disease, is defined in accordance with van Heerwarden, M. A., Smout A. J. P. M., 2000; *Diagnosis of reflux disease. Baillière's Clin. Gastroenterol.* 14, pp. 759-774.

The wording "regurgitation" is defined as the expulsion of undigested food and gastric juice.

The wording "lung disease" is defined as any deviation from or any interruption of the normal function of the lung.

The wording "laryngitis" is defined as an inflammation of the larynx, a condition with dryness and soreness of the throat, hoarseness, cough and dysphagia. The wording "chronic" is defined as persisting over a long period of time.

Asthma is an inflammatory disorder of the airways, characterized by periodic attacks of wheezing, shortness of breath, chest tightness and coughing. The wording "reflux-related asthma" is defined in accordance with Richter, J. E. 2000; *Gastroesophageal Reflux Disease and Asthma: The Two Are Directly Related. Am. J. Med.* 108 (4A), pp. 153S-158S.

In one aspect of the invention, the cannabinoid receptor agonist(s) as used in accordance with the present invention, have an effect duration of approximately 4 to 24 hours. The wording "duration" is defined as the time period from the time of onset to the time When no effect can be measured.

Within the scope of the present invention is particularly the use of cannabinoid receptor agonists falling within the four main chemical categories of cannabinoid receptor agonists. Thus, eicosanoids, and analogues thereof; classical cannabinoids and analogues thereof; non-classical cannabinoids and analogues thereof; and aminoalkylindole cannabinoids and analogues thereof, are particularly useful in accordance with the invention.

Examples of specific compounds having agonistic, indirect or partial agonistic, affinity to cannabinoid (CB) receptors, thereby being useful in accordance with the invention, are the following compounds.

I) Eicosanoid CB Receptor Agonists:
   Anandamide (commercially available from e.g. Tocris Cookson, Bristol, U.K.), which is a compound of the formula

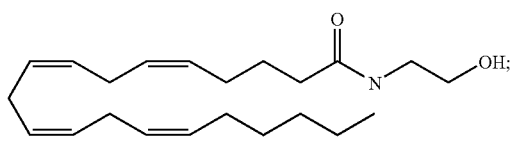

eicosa-5,8,11,14-tetraenoic acid (2-chloro-ethyl)-amide, also known as Arachidonyl-2'-chloroethylamide (ACEA, commercially available from e.g. Tocris Cookson, Bristol, U.K.); and
   eicosa-5,8,11,14-tetraenoic acid cyclopropylamide, also known as Arachidonyl cyclopropylamide (ACPA, commercially available from e.g. Tocris Cookson, Bristol, U.K.).

II) Classical CB Receptor Agonists:
   $\Delta^9$-THC ($\Delta^9$-tetrahydrocannabinol, commercially available from e.g. Sigma-Aldrich), a compound of the formula

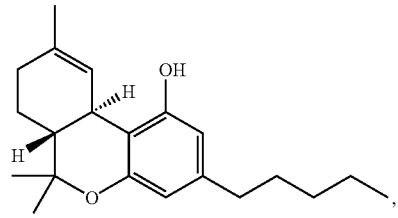

having the chemical name 6,6,9-trimethyl-3-pentyl-6a,7,8,10a-tetrahydro-6H-benzo[c]chromen-1-ol, as well as the enantiomer (−)-$\Delta^9$-tetrahydrocannabinol [(−)-$\Delta^9$-THC)]; and
   (−)-(R,R)-6,6-Dimethyl-(1,1-dimethylheptyl)-1-hydroxy-9-(hydroxymethyl)-6a,7,10,10a-tetrahydro-6H-dibenzo[b,d]pyran, [11-hydroxy-$\Delta^8$-THC-dimethylheptyl], also known as HU-210 (commercially available from e.g. Tocris Cookson, Bristol, U.K.).

III) Non-Classical CB Receptor Agonists:
   CP 55,940, a compound having the chemical name 5-(1,1-dimethyl-heptyl)-2-[5-hydroxy-2-(3-hydroxy-propyl)-cyclohexyl]phenol (commercially available from e.g. Tocris Cookson, Bristol, U.K.), and the chemical structure

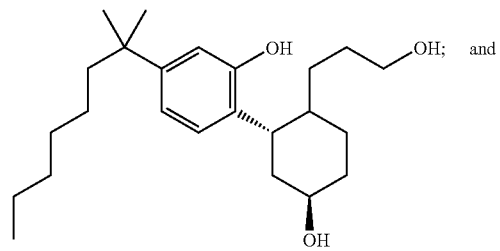

(−)-(6S,6aR,9R,10aR)-5,6,6a,7,8,9,10a-octahydro-6-methyl-3-[(R)-1-methyl-4-phenylbutoxyl]-1,9-phenanthridinediol 1-acetate, also known as L-nantradol (CP 50,556).

IV) Aminoalkylindole CB Receptor Agonists:
   WIN 55,212-2 (commercially available from e.g. Tocris Cookson, Bristol, U.K.), having the chemical structure

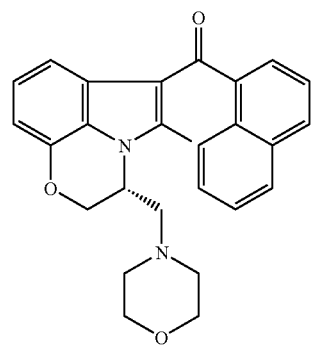

and the chemical name (2-methyl-3-morpholin-4-ylmethyl-3,4-dihydro-5-oxa-2a-aza-acenaphthylen-1-yl)-naphthalen-1-yl-methanone; and L-768,242, having the chemical name (2,3-dichloro-phenyl)-[5-methoxy-2-methyl-3-(2-morpholin-4-yl-ethyl)-indol-1-yl]-methanone, and the chemical structure

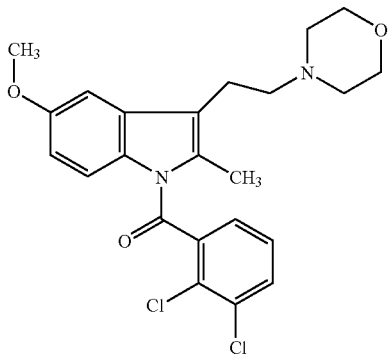

Also useful in further aspects of the present invention, are cannabinoid receptor agonists disclosed in WO 01/31169; WO 99/51560; EP 0860168; WO 97/00860; WO 01/32169, such as the compound HU-308; WO 01/28497, such as the compound AM 1703; WO 01/74763; WO 01/29007; WO 01/28557. Further cannabinoid receptor agonists which may be useful in accordance with the present invention are compounds disclosed in WO 97/29079, such as arylamides of the formula

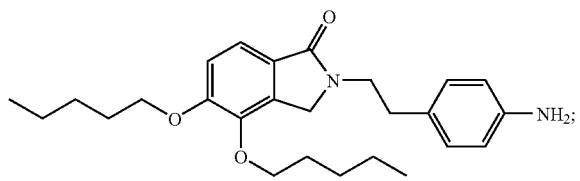

compounds as disclosed in WO 98/41519, such as pyrazoles of the formula

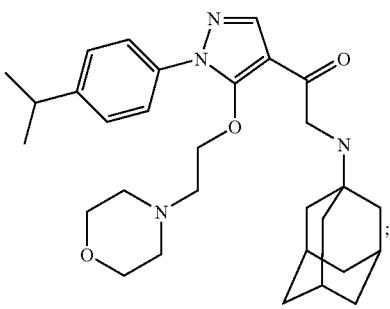

quinolines of the structure

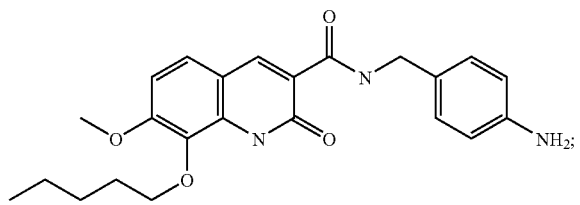

compounds as disclosed in WO 98/37061; and WO 00/10967, and more particularly therein the arylsulphonamide

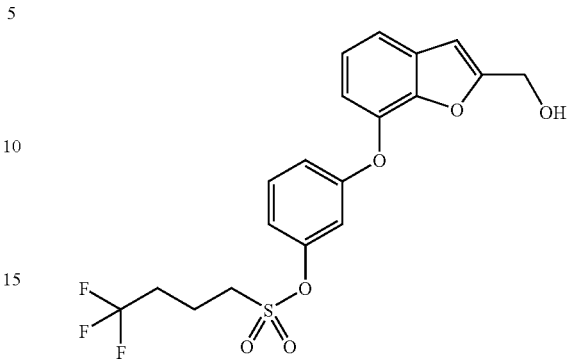

Still further compounds which may be useful in accordance with the present invention are cannabinoid receptor agonists disclosed by F. Barth in *Exp. Opin. Ther. Patents* (1998) 8(3): pp. 301-313; and cannabinoid receptor agonists disclosed by P. Goya & N. Jagerovic in *Exp. Opin. Ther. Patents* (2000) 10(10):pp. 1529-1538. The above mentioned specific cannabinoid receptor agonists, as well as the cannabinoid receptor agonists disclosed in any one of the published patent applications above, are herein incorporated by reference. This list of cannabinoid receptor agonists should not in any way be regarded as an exhaustive list limiting the scope of the invention.

Examples of indirect cannabinoid receptor agonists useful in accordance with the present invention are the compounds AM 374 (commercially available from e.g. Calbiochem-Novabiochem Corporation) and AM 404 (commercially available from e.g. Tocris Cookson, Bristol, U.K).

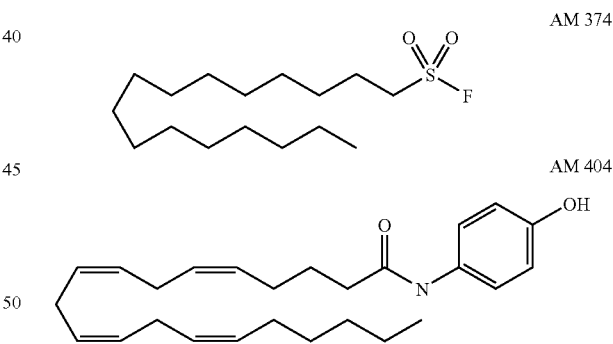

The use of pharmaceutically acceptable salts of cannabinoid receptor agonists is also within the scope of the present invention. Such salts are for example salts formed with mineral acids such as hydrochloric acid; alkali metal salts such as sodium or potassium salts; or alkaline earth metal salts such as calcium or magnesium salts.

The use of optical isomers of cannabinoid receptor agonists are also within the scope of the present invention. Cannabinoid receptor agonists having an asymmetric carbon atom are chiral compounds, and depending on the presence of asymmetric atoms, the cannabinoid receptor agonists may exist in the form of mixtures of isomers, particularly racemates, or in the form of pure isomers such as specific enantiomers.

Pharmaceutical Formulations

For clinical use, the cannabinoid receptor agonists are in accordance with the present invention suitably formulated into pharmaceutical formulations for oral administration. Also rectal, parenteral or any other route of administration may be contemplated to the skilled man in the art of formulations. Thus, the cannabinoid receptor agonists are formulated with at least one pharmaceutically and pharmacologically acceptable carrier or adjuvant. The carrier may be in the form of a solid, semi-solid or liquid diluent.

In the preparation of oral pharmaceutical formulations in accordance with the invention, the cannabinoid receptor agonist(s) to be formulated is mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or compressed into tablets.

Soft gelatine capsules may be prepared with capsules containing a mixture of the active compound or compounds of the invention, vegetable oil, fat, or other suitable vehicle for soft gelatine capsules. Hard gelatine capsules may contain the active compound in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance(s) mixed with a neutral fat base; (ii) in the form of a gelatine rectal capsule which contains the active substance in a mixture with a vegetable oil, paraffin oil, or other suitable vehicle for gelatine rectal capsules; (iii) in the form of a ready-made micro enema; or (iv) in the form of a dry micro enema formulation to be reconstituted in a suitable solvent just prior to administration.

Liquid preparations for oral administration may be prepared in the form of solutions, syrups or suspensions containing the active compound and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

In one aspect of the present invention, the cannabinoid receptor agonist may be administered once or twice daily, depending on the severity of the patient's condition. A typical daily dose of the cannabinoid receptor agonist is within the range of from 0.1-500 mg (including 0.1 and 500 mg), such as 0.1-100 mg, but this will depend on various factors such as the route of administration, the age and weight of the patient as well as of severity of the patient's condition.

Biological Evaluation

Screening for Compounds Active Against TLESR

Adult Labrador retrievers of both genders, trained to stand in a Pavlov sling, are used. Mucosa-to-skin esophagostomies are formed and the dogs are allowed to recover completely before any experiments are done.

Motility Measurement

In brief, after fasting for approximately 17 h with free supply of water, a multilumen sleeve/sidehole assembly (Dentsleeve, Adelaide, South Australia) is introduced through the esophagostomy to measure gastric, lower esophageal sphincter (LES) and esophageal pressures. The assembly is perfused with water using a low-compliance manometric perfusion pump (Dentsleeve, Adelaide, South Australia). An air-perfused tube is passed in the oral direction to measure swallows, and an antimony electrode monitored pH, 3 cm above the LES. All signals are amplified and acquired on a personal computer at 10 Hz.

When a baseline measurement free from fasting gastric/LES phase III motor activity has been obtained, placebo (0.9% NaCl) or test compound is administered intravenously (i.v., 0.5 ml/kg) in a foreleg vein. Ten min after i.v. administration, a nutrient meal (10% peptone, 5% D-glucose, 5% Intralipid, pH 3.0) is infused into the stomach through the central lumen of the assembly at 100 ml/min to a final volume of 30 ml/kg. Immediately following the meal, air is insufflated at 40 ml/min. The experimental time from start of nutrient infusion to end of air insufflation is 45 min. The procedure has been validated as a reliable means of triggering TLESRs.

TLESRs is defined as a decrease in lower esophageal sphincter pressure (with reference to intragastric pressure) at a rate of >1 mmHg/s. The relaxation should not be preceded by a pharyngeal signal ≦2 s before its onset in which case the relaxation is classified as swallow-induced. The pressure difference between the LES and the stomach should be less than 2 mmHg, and the duration of the complete relaxation longer than 1 s.

EXAMPLES

Example 1

The aminoalkylindole cannabinoid WIN 55,212-2, purchased from Tocris Cookson (Bristol, U.K.), was tested on Adult Labrador retrievers of both genders in accordance with the test model described above.

Inhibition of the number of TLESRs was calculated with regard to the five preceding control experiments for each dog, and the results as set out in Table 1 below were achieved.

TABLE 1

| COMPOUND | DOSE [mg/kg] | % INHIBITION ± SEM (N) |
|---|---|---|
| WIN 55,212-2 | 0.003 | 20 ± 18 (4) |
| WIN 55,212-2 | 0.01 | 70 ± 10 (4) |
| WIN 55,212-2 | 0.03 | 82 ± 1 (4) |

N = number of dogs tested.;
SEM = Standard Error of Mean

Example 2

The aminoalkylindole cannabinoid L768,242 was synthesized at AstraZeneca R&D Mölndal, Sweden, according to the procedure described in *Bioorg. & Afed. Chein. Lett.* (1996); Vol. 6, No. 19, pp. 2263-2268, and tested as in Example 1 above.

Inhibition of the number of TLESRs was calculated with regard to the five preceding control experiments for each dog, and the results as set out in Table 2 below were achieved.

TABLE 2

| COMPOUND | DOSE [µmol/kg] | % INHIBITION ± SEM (N) |
|---|---|---|
| L-768,242 | 0.3 | 8 ± 21 (4) |
| L-768,242 | 1 | 44 ± 6 (5) |
| L-768,242 | 5 | 63 ± 5 (4) |
| L-768,242 | 7 | 76 ± 12 (3) |

N = number of dogs tested.;
SEM = Standard Error of Mean

Example 3

The pyrazole SR141716A (CB1 antagonist) was synthesized at AstraZeneca R&D Mölndal, Sweden, according to the procedure described in *J. Chem. Soc., Chem. Commun.* (1995); No. 15, pp 1549-1560, and tested as in Example 1 above.

Stimulation of the number of TLESRs was calculated with regard to the five preceding control experiments for each dog, and the results as set out in Table 3 below were achieved.

TABLE 3

| COMPOUND | DOSE [µmol/kg] | % STIMULATION ± SEM (N) |
|---|---|---|
| SR141716A | 0.22 | 43 ± 16 (6) |

N = number of dogs tested.;
SEM = Standard Error of Mean

The results in the example 3 above, indicate a tonic activity of endocannabinoids mediating suppression of TLESRs, which in turn suggest that indirect cannabinoid agonists (inhibitors of FAAH and ANT) are useful for the inhibition of TLESRs, and thus for treatment of GERD.

The results shown in the Examples 1-3 above, indicate that cannabinoid receptor agonists are useful for the inhibition of TLESRs, and thus for the treatment of GERD.

The invention claimed is:

1. A method for the inhibition of transient lower esophageal sphincter relaxations (TLESRs), the method comprising administering a therapeutically effective amount of a compound which is a cannabinoid receptor agonist, a pharmaceutically acceptable salt of the compound, an optical isomer of the compound, or a pharmaceutically acceptable salt of the optical isomer, to a patient suffering from gastroesophageal reflux disease.

2. A method for the treatment of gastroesophageal reflux disease (GERD), the method comprising administering a therapeutically effective amount of a compound which is a cannabinoid receptor agonist, a pharmaceutically acceptable salt of the compound, an optical isomer of the compound, or a pharmaceutically acceptable salt of the optical isomer, to a patient suffering from gastroesophageal reflux disease.

3. A method for the inhibition of reflux of gastric juice, the method comprising administering a therapeutically effective amount of a compound which is a cannabinoid receptor agonist, a pharmaceutically acceptable salt of the compound, an optical isomer of the compound, or a pharmaceutically acceptable salt of the optical isomer, to a patient suffering from gastroesophageal reflux disease.

4. A method for the treatment or inhibition of regurgitation of gastric juice, the method comprising administering a therapeutically effective amount of a compound which is a cannabinoid receptor agonist, a pharmaceutically acceptable salt of the compound, an optical isomer of the compound, or a pharmaceutically acceptable salt of the optical isomer, to a patient suffering from gastroesophageal reflux disease.

5. The method according to claim 4, wherein the regurgitation to be treated or inhibited is regurgitation in infants.

6. The method according to any one of claims 1-5, wherein the daily dose of the cannabinoid receptor agonist is within the range of from 0.1-500 mg.

7. The method according to any one of claims 1-5, wherein the cannabinoid receptor agonist is a CB1-receptor-selective cannabinoid receptor agonist.

8. The method according to any one of claims 1-5, wherein the cannabinoid receptor agonist is a CB2-receptor-selective cannabinoid receptor agonist.

9. The method according to any one of claims 1-5, wherein the cannabinoid receptor agonist is an eicosanoid.

10. The method according to claim 9, wherein the cannabinoid receptor agonist is selected from the group consisting of Anandamide; Arachidonyl-2'-chloroethylamide; and Arachidonyl cyclopropylamide.

11. The method according to any one of claims 1-5, wherein the cannabinoid receptor agonist is a classical cannabinoid.

12. The method according to claim 11, wherein the cannabinoid receptor agonist is $\Delta^9$-tetrahydrocannabinol; or 11-hydroxy-$\Delta^8$-THE-dimethylheptyl.

13. The method according to any one of claims 1-5, wherein, the cannabinoid receptor agonist is a non-classical cannabinoid.

14. The method according to claim 13, wherein the cannabinoid receptor agonist is:

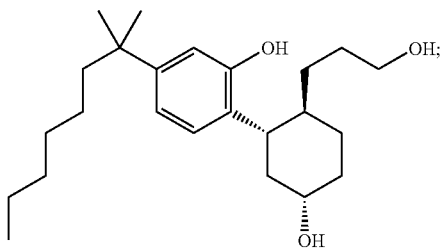

or L-nantradol: (-)-(6S,6aR,9R,10aR)-5,6,6a7,8,9,10a-octahydro-6-methyl-3-[(R)-1-methyl-4-phenylbutoxyl]-1,9-phenanthridinediol1-acctate.

15. The method according to any one of claims 1-5, wherein the cannabinoid receptor agonist is an aminoalkylindole cannabinoid.

16. The method according to claim 15, wherein the cannabinoid receptor agonist is:
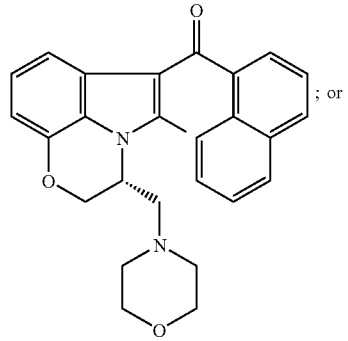 ; or
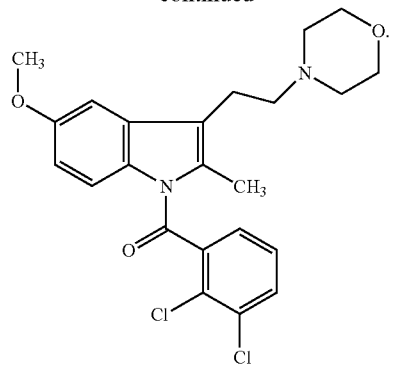
* * * * *